US00PP15998P2

(12) United States Plant Patent
Katerberg

(10) Patent No.: US PP15,998 P2
(45) Date of Patent: Sep. 27, 2005

(54) ***BUXUS* PLANT NAMED 'KATERBERG'**

(50) Latin Name: *Buxus sempervirens*
Varietal Denomination: Katerberg

(75) Inventor: Gerard Katerberg, Muskegon, MI (US)

(73) Assignee: Spring Meadow Nursery, Inc., Grand Haven, MI (US)

( * ) Notice: Subject to any disclaimer, the term of this patent is extended or adjusted under 35 U.S.C. 154(b) by 40 days.

(21) Appl. No.: 10/878,429

(22) Filed: Jun. 28, 2004

(51) Int. Cl.[7] ..... A01H 5/00
(52) U.S. Cl. ..... Plt./226
(58) Field of Search ..... Plt./226

*Primary Examiner*—Anne Marie Grunberg
*Assistant Examiner*—Annette H Para
(74) *Attorney, Agent, or Firm*—C. A. Whealy

(57) ABSTRACT

A new and distinct *Buxus* plant named 'Katerberg', characterized by its compact and mounded plant habit; freely branching habit and short internodes; dense and bushy plant form; attractive green foliage color; and good low temperature tolerance.

1 Drawing Sheet

Botanical classification/cultivar designation: *Buxus sempervirens* cultivar Katerberg.

BACKGROUND OF THE INVENTION

The present invention relates to a new and distinct cultivar of *Buxus,* botanically known as *Buxus sempervirens,* commercially known as Boxwood, and hereinafter referred to by the name 'Katerberg'.

The new *Buxus* is a naturally-occurring branch mutation of the *Buxus sempervirens* cultivar Welleri, not patented. The new *Buxus* was discovered and selected by the Inventor in a controlled environment in Grand Haven, Mich. in 1990, as a single branch on a single plant within a population of plants of the cultivar Welleri.

Asexual reproduction of the new *Buxus* by hardwood cuttings in a controlled environment in Grand Haven, Mich. since 1991, has shown that the unique features of this new *Buxus* are stable and reproduced true to type in successive generations.

SUMMARY OF THE INVENTION

The cultivar Katerberg has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Katerberg'. These characteristics in combination distinguish 'Katerberg' as a new and distinct cultivar of *Buxus:*

1. Compact and mounded plant habit.
2. Freely branching habit and short internodes, dense and bushy plant form.
3. Attractive green foliage color.
4. Good low temperature tolerance.

Plants of the new *Buxus* are most similar to plants of the parent, the cultivar Welleri. Plants of the new *Buxus* differ from plants of the cultivar Welleri in plant form and branching habit as plants of the cultivar Welleri are more upright, open, not as freely branching and have a looser branching structure than plants of the new *Buxus.* Plants of the new *Buxus* have smaller and lighter green-colored leaves than plants of the cultivar Welleri. In addition, plants of the new *Buxus* grow slower than plants of the cultivar Welleri.

Plants of the new *Buxus* can be compared to plants of the cultivar Green Ice, disclosed in U.S. Plant Pat. No. 10,773. Plants of the new *Buxus* are more compact and grow slower than plants of the cultivar Green Ice.

BRIEF DESCRIPTION OF THE PHOTOGRAPH

The accompanying colored photograph illustrates the overall appearance of the new *Buxus,* showing the colors as true as it is reasonably possible to obtain in colored reproductions of this type. Colors in the photograph may differ slightly from the color values cited in the detailed botanical description which accurately describe the colors of the new *Buxus.*

The photograph comprises a side perspective view of a typical plant of 'Katerberg' grown in an outdoor nursery.

DETAILED BOTANICAL DESCRIPTION

The aforementioned photograph and following observations and measurements describe plants grown in Grand Haven, Mich., in an outdoor nursery during the winter and spring and under conditions which closely approximate commercial production. Plants were about six years old when the photograph and the description were taken. In the description color references are made to The Royal Horticultural Society Colour Chart, 1995 Edition, except where general terms of ordinary dictionary significance are used.

Botanical classification: *Buxus sempervirens* cultivar Katerberg.

Parentage: Naturally-occurring branch mutation of the *Buxus sempervirens* cultivar Welleri, not patented.

Propagation:

*Type.*—By hardwood cuttings.

*Time to initiate roots.*—About one month at 20° C.

*Time to produce a rooted young plant.*—About one year at 25° C.

*Root description.*—Thick; creamy white in color.

*Rooting habit.*—Freely branching.

Plant description:

*Plant type.*—Perennial evergreen shrub.

*Plant form and growth habit.*—Compact and mounded plant habit. Plants roughly spherical in shape. Freely branching habit, about 2,100 lateral branches per plant; short internodes; dense and bushy plant form. Moderately vigorous.

*Plant height.*—About 58 cm.

*Plant diameter* (*area of spread*).—About 80 cm.

*Lateral branch description.*—Length: About 18 cm. Diameter: About 3 mm. Internode length: About 9 mm. Aspect: Upright to outward. Strength: Strong. Texture: Smooth, glabrous. Color: 143A.

*Foliage description.*—Arrangement: Opposite, simple. Length: About 2.2 cm. Width: About 7 mm. Shape: Elliptic. Apex: Acute. Base: Cuneate. Margin: Entire. Texture, upper and lower surfaces: Smooth, glabrous; thick. Venation pattern: Pinnate. Color: Developing leaves, upper surface: 152A to 152B. Developing leaves, lower surface: 152B. Fully expanded leaves, upper surface: 136A. Fully expanded leaves, lower surface: 152A. Venation, upper surface: 156A. Venation, lower surface: 152A. Petiole: Length: About 1 mm. Diameter: About 1 mm. Texture, upper and lower surfaces: Smooth, glabrous. Color, upper surface: 136A. Color, lower surface: 152A.

Flower description: Flower development has not been observed on plants of the new *Buxus*.

Disease/pest resistance: Plants of the new *Buxus* have been observed to be relatively resistant to pests, such as leaf miners, psyllid and mites. Plants of the new *Buxus* have not been observed to be resistant to pathogens and other pests common to *Buxus*.

Temperature performance: Plants of the new *Buxus* have been observed to be tolerant to temperatures ranging from −27° C. to 34° C.

It is claimed:

1. A new and distinct *Buxus* plant named 'Katerberg', as illustrated and described.

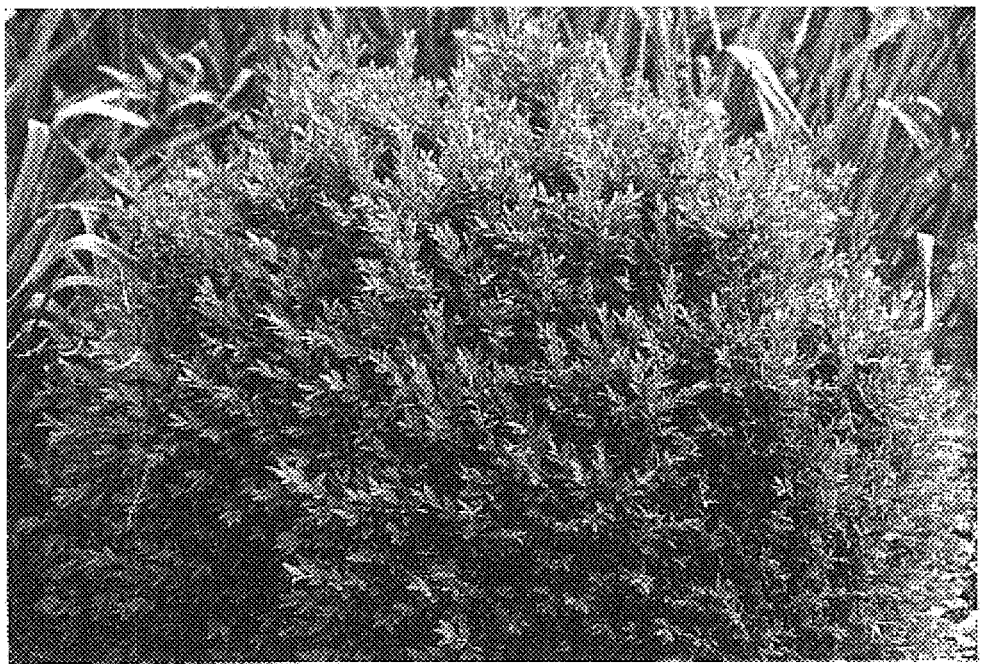

* * * * *